(12) United States Patent
Slemon et al.

(10) Patent No.: US 6,191,856 B1
(45) Date of Patent: Feb. 20, 2001

(54) OPTICAL INSPECTION DEVICE

(75) Inventors: Charles S. Slemon, Encinitas; W. James Frandsen, San Diego; James John Glover, La Mesa, all of CA (US)

(73) Assignee: Volution, San Diego, CA (US)

( * ) Notice: Under 35 U.S.C. 154(b), the term of this patent shall be extended for 0 days.

(21) Appl. No.: 09/553,986

(22) Filed: Apr. 20, 2000

Related U.S. Application Data

(63) Continuation-in-part of application No. 09/305,608, filed on May 5, 1999.

(51) Int. Cl.[7] .................................................. G01N 21/86
(52) U.S. Cl. ........................................ 356/375; 250/559.29
(58) Field of Search ........................ 356/375; 250/559.29

(56) References Cited

U.S. PATENT DOCUMENTS

| | | | |
|---|---|---|---|
| 4,507,834 | * | 4/1985 | Chen et al. .......................... 29/26 R |
| 4,876,455 | | 10/1989 | Sanderson et al. . |
| 5,004,930 | * | 4/1991 | Gremaud et al. ..................... 250/561 |
| 5,005,978 | * | 4/1991 | Skunes et al. ....................... 356/372 |
| 5,106,183 | | 4/1992 | Yoder, Jr. . |
| 5,293,048 | * | 3/1994 | Skunes et al. ....................... 250/561 |
| 5,404,021 | * | 4/1995 | Mangano et al. ..................... 250/561 |
| 5,412,476 | * | 5/1995 | Marantette ........................... 356/375 |
| 5,477,332 | | 12/1995 | Stone et al. . |

* cited by examiner

Primary Examiner—Richard A. Rosenberger
(74) Attorney, Agent, or Firm—Nydegger & Associates

(57) ABSTRACT

An optical device for establishing a spatial orientation for a drill bit includes at least three light sources and two cameras. The first light source is used to silhouette the drill bit; a second light source is used to generate a reflection from a primary facet of the drill bit; and a third light source is used to generate a reflection from the margin of the drill bit. In sequence, the first camera responds to the first light source to establish an axial position for the drill bit on the axis. The second camera then responds to the second light source to establish a gross rotational position for the drill bit on its axis. Finally, the first camera is again used. This time it establishes a precise rotational position for the drill bit on its axis to establish the spatial orientation for the drill bit.

20 Claims, 2 Drawing Sheets

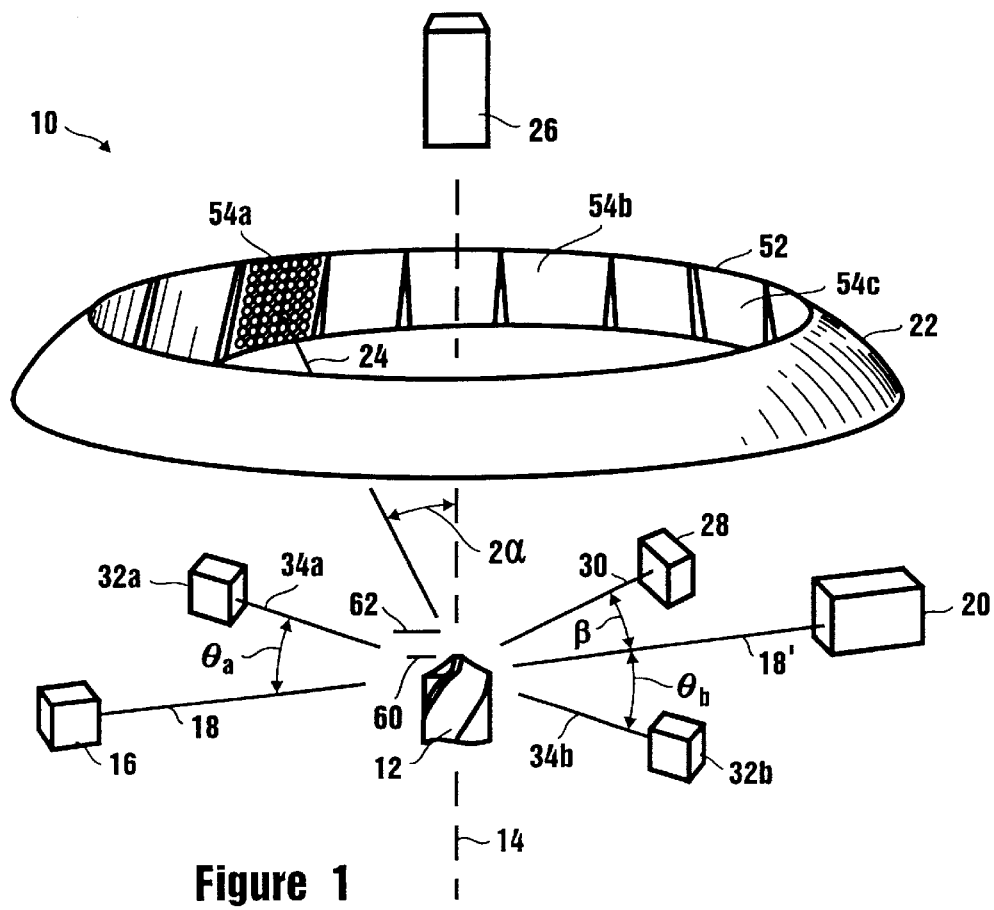
Figure 1
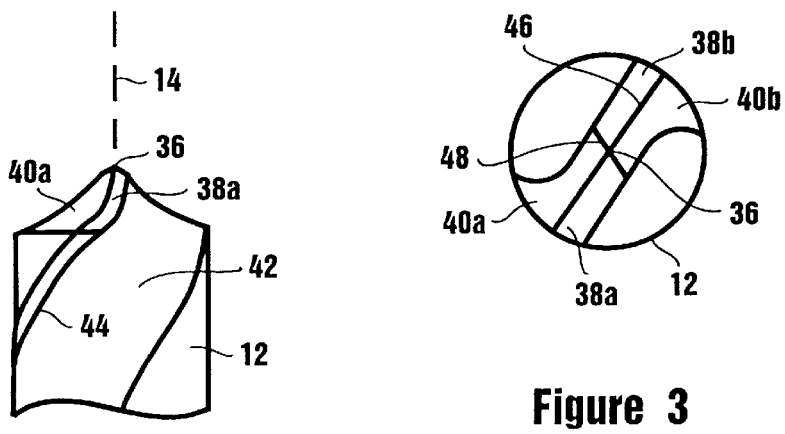
Figure 2
Figure 3

OPTICAL INSPECTION DEVICE

This application is a continuation-part of application U.S. Ser. No. 09/305,608, filed May 5, 1999, which is currently pending. The contents of application U.S. Ser. No. 09/305,608 are incorporated herein by reference.

FIELD OF THE INVENTION

The present invention pertains generally to inspection systems and methods. More particularly, the present invention pertains to systems and methods for inspecting and evaluating machine tools. The present invention is particularly, but not exclusively, useful as a device and a method for using same which employs optical techniques for selectively inspecting and evaluating the operational serviceability of drill bits.

BACKGROUND OF THE INVENTION

A "drill bit" is defined as a removable drilling or boring tool for use in a brace, drill press, or the like, and will generally be of a type that is classified either as an auger or as a straight shank drill bit. Of particular interest for the present invention is the so-called straight shank drill bit.

In order to drill or bore a hole into a surface with a straight shank drill bit, the drill bit is rotated relative to the surface by a brace or drill press. Sharp edges on the front or tip of the drill bit then cut into the surface. Due to the drill bit's configuration, the material that is cut as the drill bit is rotated is removed so that the result is a clean hole in the surface. Not surprisingly, with extended use, a drill bit can become worn. Thus, periodic screening may be necessary to determine whether the drill bit can be reshaped and reused, or must be discarded. Whenever a large number of particularly small drill bits are involved, the inspection and selection process for screening the drill bits can become quite labor intensive and very time consuming.

It happens that there is a standard configuration for straight shank drill bits. Importantly, although the particular dimensions of drill bits and the exact angles between respective component parts of different drill bits will vary, all straight shank drill bits generally have the same general configuration. Consequently, the component parts of the drill bit always have the same relationship relative to each, and they always have the same relationship relative to the longitudinal axis of the drill bit. Specifically, at the front end, or tip, of the drill bit are a pair of component parts more commonly referred to as primary facets. These primary facets are generally flat surfaces, and they each have a side which is aligned along a common diameter (extension line). Further, the primary facets are on opposite sides of the drill bit's longitudinal axis, and they are on opposite sides of their common diameter (extension line). Depending on the model of the drill bit, a normal to the primary facets will be inclined to the longitudinal axis of the drill bit by an angle $\alpha$.

In addition to the primary facets mentioned above, the tip of the drill bit is also formed with a pair of diametrically opposed secondary facets that are each juxtaposed with a respective primary facet. Additionally, the drill bit has a pair of helical shaped flutes that continue from a respective secondary facet and extend generally along the length of the drill bit shank parallel to the axis. Each of these flutes is characterized by a margin that borders the flute along the length of the drill bit. For operational purposes, however, of all the component parts of the drill bit, it is the primary facets that face the most wear and are, therefore, of most concern. As indicated above, however, the primary facets are positioned in a rather complex geometrical orientation on the drill bit. Accordingly, any regrinding of the primary facets that may be necessary in order to maintain the serviceability of the drill bit must be done with a great deal of precision and care.

There are many optical techniques which have been used for purposes of inspecting and evaluating various items. While some of these techniques merely require adequate illumination of the item, others can involve highly sophisticated interference, absorption or specular analysis. In each case, some aspect or characteristic of light plays an important role. For the present invention, the characteristic of light that is of most importance is reflection.

In general, the reflection of light from an object can be classed as being either specular reflection or non-specular, diffuse reflection. In the case of non-specular or diffuse reflection, the reflection of light from a rough surface results in a scattering of the light wave components. On the other hand, the specular reflection of light occurs when a wavefront of light is diverted from a polished surface, so that the angle of the incident wave to the normal at the point of reflection is the same as that of the reflected wave. For irregular shaped objects, such as a drill bit, the specular reflection of light can be observed from predetermined surfaces. Specifically, depending on the known location of a light source, and the expected location of a particular surface, a detector (such as a camera) can be appropriately positioned to receive a specular reflection from the surface. The presence or absence of the specular reflection can then be used as intelligence for purposes of orienting or inspecting the item on which the surface is located.

In light of the above, it is an object of the present invention to provide an optical device and a method which uses specular reflections from a drill bit to establish a spatial orientation for the drill bit. Another object of the present invention is to provide an optical device and a method which uses specular reflections from a drill bit, in concert with other illumination techniques, to measure dimensions of the drill bit. Still another object of the present invention is to provide an optical device and a method which uses specular reflections to inspect for irregularities in selected surfaces and boundaries of these surfaces. Yet another object of the present invention is to provide an optical device and a method which is easy to use, relatively simple to manufacture, and comparatively cost effective.

SUMMARY OF THE PREFERRED EMBODIMENTS

In accordance with the present invention, an optical device for establishing a predetermined spatial orientation for a drill bit includes three separate light sources which are used for selectively illuminating the drill bit in at least three different illumination schemes. The device also includes two camera systems that are used for creating images of the drill bit under the different illumination schemes. Specifically, the images of the drill bit are used to establish a spatial orientation for the drill bit in which subsequent grinding or inspection of the drill bit can be accomplished. As contemplated by the present invention, the drill bit will define a longitudinal axis and it will have a pair of diametrically opposed primary facets. Normals (i.e. perpendicular lines) to these primary facets will be inclined at a known angle $\alpha$ to the axis. Specifically, as determined for the present invention, $\alpha = \cos^{-1}(1/\sqrt{(1+\tan^2(\phi)+\tan^2(\psi))})$ where, in a Cartesian coordinate system, $\alpha$ is an angle with the z axis (the longitudinal axis), $\phi$ is an angle of rotation about the x axis, and ψ is an angle of rotation about the y axis. Additionally, the drill bit will have margins which border helical flutes that extend generally along the length of the drill bit parallel to the axis.

Insofar as the light sources are concerned, it is to be appreciated that the present invention does not use diffuse light sources. Instead, semicollimated light sources are used. One light source (the first light source) generates a light beam that is directed perpendicular to the drill bit for the purpose of silhouetting the drill bit. Another light source (the second light source) is used to generate reflections from the primary facets of the drill bit. Still, another light source (the third light source) is used to generate reflections from the margin of the drill bit. Using these various illumination schemes, the device of the present invention creates camera images that indicate how the drill bit needs to be moved in order to acquire the desired spatial orientation.

One camera in the optical device of the present invention (the first camera) views the drill bit from a position that is directly opposite the drill bit from the silhouetting light source. In this position, this camera creates a shadow silhouette image of the drill bit that can be used to establish the axial position of the drill bit. Also, the position of this camera allows it to create images of a margin on the drill bit by using light that has been reflected from the drill bit margin. Another camera (the second camera) is positioned on an extension of the drill bit axis, and is used to create images of the drill bit facets that are formed by light that has been reflected along the axis.

While the silhouetting light source (first light source) and the light source that is used to illuminate the drill bit margins (third light source) can each be a single LED, the light source that is used to illuminate the primary facets of the drill bit (second light source) is more complex. Specifically, this light source (second light source) includes many individual light sources (LEDs) which are positioned and operated, relative to each other, in a specific manner.

In detail, the light source that is used to illuminate the primary facets of the drill bit (second light source) includes a plurality of arrays (e.g. sixteen arrays) that are formed as a ring. Further, each array in the ring is slightly tilted relative to a central axis and includes a plurality of individual light sources (LEDs) that are arranged in a plurality of rows (e.g. seven rows). Geometrically, the arrays are positioned around the ring in diametrically opposed pairs (i.e. sixteen arrays provide eight pairs), and the ring is oriented in a plane with each row of light sources (LEDs), in all of the arrays, oriented substantially perpendicular to the central axis. Further, each LED in each row directs a respective light beam toward the central axis at an angle, $2\alpha$. Recall, the primary facets have normals that are inclined to the axis at an angle, $\alpha$. Thus, light from the LEDs that is reflected by the primary facets will travel substantially along the axis of the drill bit.

Preferably, as indicated above, there will be around seven rows of LEDs in each array. All of the LEDs in a same row can then be collectively directed to accommodate a specific angle, $2\alpha$. Specifically, it is important that this angle, $2\alpha$ correspond to the particular primary facet configuration that is being imaged. Stated differently, because the primary facets of different drill bits can have different angle configurations (e.g. $\alpha_1, \alpha_2, \alpha_3 \ldots \alpha_7$) the LEDs in the various rows of the array will direct light onto the primary facet at respectively different angles (e.g. $2\alpha_2, 2\alpha_2, 2\alpha_3 \ldots 2\alpha_7$). For discussion purposes, only three such rows and three correspondingly different primary facet configurations will be described. Accordingly, a first row of LEDs will direct light toward the drill bit at an angle $2\alpha_1$ for reflection from primary facets that have a normal inclined at an angle $\alpha_1$ from the axis. Similarly, a second row will direct light toward the drill bit at an angle $\alpha_2$, for reflection from primary facets that have a normal inclined at an angle $\alpha_2$ from the axis, and a third row will direct light toward the drill bit at an angle $2\alpha_3$ for reflection from primary facets having a normal inclined at an angle $\alpha_3$ from the axis.

In the operation of the present invention, a drill bit is advanced to an axial position in front of the silhouetting light source. The resultant shadow of the drill bit is then used to create a camera image which identifies the length of the drill bit and indicates the axial movement necessary to bring the drill bit into focus. Next, a row of LEDs is selected which corresponds to the angle $\alpha_n$ (n=1, 2, 3 . . . 7) configuration of the drill bit's primary facets. Specifically, the LEDs in this row will direct light toward the primary facets at an angle $2\alpha_n$. The same rows, in each of the different pairs of arrays in the ring, are then selectively illuminated until the pair giving the clearest image of the primary facets is identified. Using this image, the drill bit is rotated to establish a gross rotational position for the drill bit on the axis that will be accurate to within approximately eight degrees (i.e. ±40°). The light source for illuminating the margin is then activated to fine tune the rotation of the drill bit. Specifically, by using reflections from the margin of the drill bit, the drill bit can be rotated into a precise rotational position which is accurate to within approximately one half of a degree (i.e. ±0.250°). The spatial orientation of the drill bit is thus established.

Once the spatial orientation of the drill bit is established, the drill bit can be moved to a dimensionally calibrated grinding wheel where the primary facets can be ground to sharpen the drill bit. After grinding, the drill bit can be returned to a predetermined spatial orientation in the optical device of the present invention where both the primary and secondary facets of the drill bit can be inspected. The drill bit can then be returned to service.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 1 is a perspective schematic view of the optical system of the present invention;

FIG. 2 is a side view of a drill bit;

FIG. 3 is a front view of the drill bit shown in FIG. 2;

DESCRIPTION OF THE PREFERRED EMBODIMENT

Figure 4:
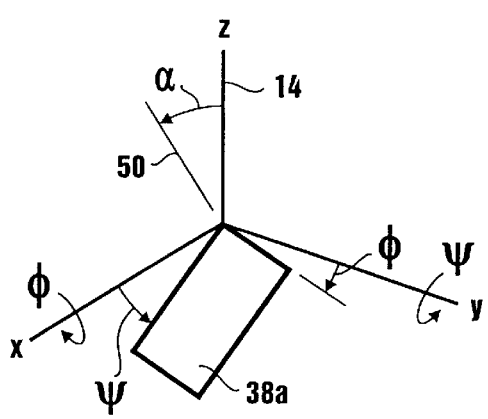
FIG. 4 is a cartesian coordinate system describing the angel $\alpha$ as used for the present invention.

Referring initially to FIG. 1 a device in accordance with the present invention is shown and is generally designated 10. As shown, the device 10 is used to sequentially illuminate a drill bit 12 from different predetermined locations. The device 10 then receives the resultant reflections from the drill bit 12 to accurately and precisely position the drill bit 12. For reference purposes, the drill bit 12 is shown to have a longitudinal axis 14 which extends along the length of the drill bit 12.

In FIG. 1 the device 10 is shown to include a light source 16 that directs a beam of light along the beam path 18. As intended for the device 10, the beam path 18 will be substantially perpendicular to the axis 14 and will be located opposite the drill bit 12 from a camera 20. Consequently, upon activation of the light source 16, the camera 20 will receive a silhouette image of the drill bit 12. Preferably, the light source 16 is an LED of a type well known in the pertinent art.

As also seen in FIG. 1, the device 10 includes a light source 22 that is positioned to surround the axis 14. For the present invention, the light source 22 selectively directs light along beam paths 24 that are azimuthally oriented around the axis 14 (the beam path 24 in FIG. 1 is only exemplary). Depending on the configuration of the drill bit 12, and the particular orientation of the beam path 24, the light from light source 22 will be reflected from the drill bit 12 in a direction along the axis 14 toward a camera 26. Thus, the camera 26 will receive a specular reflection from the drill bit 12.

FIG. 1 also shows a light source 28 that is positioned to direct light toward the drill bit 12 along a beam path 30 that is substantially perpendicular to the axis 14. As intended for the present invention, the light from light source 28 will be reflected toward the camera 20 along the beam path 18'. Note that the beam path 18' is effectively an extension of the beam path 18, and that the beam path 30 is coplanar with the beam path 18' and forms an angle β therewith. Further, the device 10 includes a pair of light sources 32a and 32b that, respectively, direct light along colinear beam paths 34a and 34b for reflection from the drill bit 12. The beam paths 34a and 34b are both substantially perpendicular to the axis 14 and the reflection of these beam paths 34a and 34b is directed from drill bit 12 along the axis 14 and toward camera 26. As shown, the beam path 34a forms an angle $\theta_a$ with beam path 18 and the beam path 34b forms an angle $\theta_b$ with the beam path 18'. For purposes of the present invention, the light source 28 and the light sources 32a and 32b are preferably LEDs.

In FIG. 2, the component parts of a drill bit 12 are shown in more detail. Specifically, as shown, a typical drill bit 12 is formed with a tip 36 that has two primary facets 38a and 38b, and two secondary facets 40a and 40b. Additionally, there are helical shaped flutes 42 which extend generally along the shank of the drill bit 12 and are bordered by a margin 44. As perhaps best seen in FIG. 3, both of the primary facets 38a and 38b are positioned astride a diametrical extension line 46 and are located opposite the tip 36 from each other. The secondary facets 40a and 40b are juxtaposed respectively with primary facets 38a and 38b and are also positioned astride the extension line 46. Another diametrical extension line 48 also separates the facets such that primary facet 38a is opposite extension line 46 from the secondary facet 40a and is opposite extension line 48 from the secondary facet 40b. Similarly, primary facet 38b is opposite extension line 46 from the secondary facet 40b and is opposite extension line 48 from the secondary facet 40a.

It is an important aspect of the present invention that any normal 50 to a primary facet 38 will be inclined at an angle α to the axis 14. Specifically, the angle α is inclined such that $\alpha=\cos_{-1}(1/\sqrt{(1+\tan^2(\phi)+\tan^2(\psi))})$ where, in a Cartesian coordinate system, α is an angle with the z axis, φ is an angle of rotation about the x axis, and ψ is an angle of rotation about the y axis. A geometrical representation of the relationship between the angles α, φ and ψ is shown in FIG. 4. As appreciated by the present invention, the angle α can vary from one configuration for drill bit 12 to another. Importantly, however, each drill bit 12 will have an identifiable angle α. Consequently, in order for light to be specularly reflected from a primary facet 38, along the axis 14 toward camera 26, it is necessary that the light source 22 be able to direct the beam path 24 toward a primary facet 38 with an angle of incidence equal to α. Specifically, in accordance with the general laws of reflection which require that the angle of incidence (i.e. an angle α between beam path 24 and normal 50) be equal to the angle of reflection (i.e. an angle α between normal 50 and the axis 14), the beam path 24 needs to be inclined at an angle 2α relative to the axis 14 in order for there to be a specular reflection from primary facet 38 along the axis 14. To accomplish this, the light source 22 of the device 10 is really a plurality of individual light sources.

Returning to FIG. 1, it is seen that the light source 22 is formed as a ring 52 which surrounds and is centered on the axis 14. Further, the ring 52 generally defines a plane which is perpendicular to the axis 14. As best seen in FIG. 1, the light source 22 includes a plurality of tilted arrays 54. Preferably, there are sixteen separate arrays 54 in light source 22 (of which the arrays 54a, 54b and 54c are exemplary) that are arranged as diametrically opposed pairs. Accordingly, there are preferably eight such pairs of the arrays 54.

Figure 5:
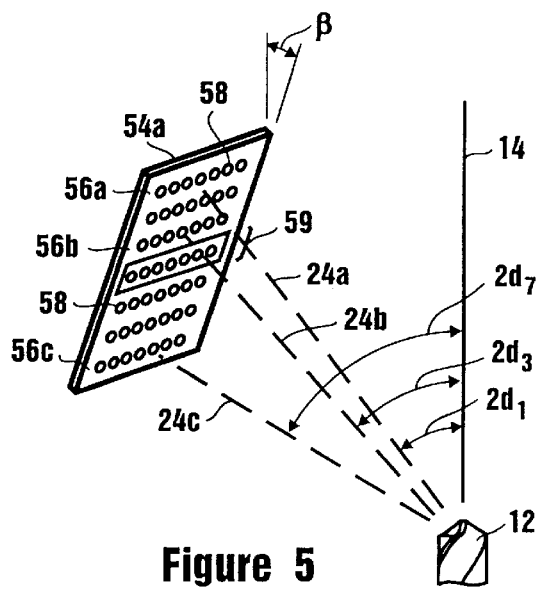
FIG. 5 is a perspective schematic view showing the relationship between an array of light sources, as used for the present invention, and the respective angle $\alpha_n$ between selected rows of light sources in the array and the drill bit.

By cross referencing FIG. 5 with FIG. 1, it will be appreciated that each of the arrays 54 includes a plurality of individual light sources 58 that are respectively arranged in rows 56 (of which the rows 56a, 56b and 56c are only exemplary). Importantly, each row 56 is oriented to be substantially perpendicular to the axis 14, and all of the individual light sources 58 in a single row 56 are positioned to direct light along beam paths 24 that are inclined at an angle $2\alpha_n$ to the axis 14. For example, all of the individual light sources 58 in row 56a of the array 54a will direct light generally along the beam path 24a which is inclined at an angle $2\alpha_1$ to the axis 14. Similarly, all of the individual light sources 58 in row 56b of the array 54a will direct light generally along the beam path 24b which is inclined at an angle $2\alpha_3$ to the axis 14. Likewise, all of the individual light sources 58 in row 56c of the array 54a will direct light generally along the beam path 24c which is inclined at an angle $2\alpha_7$ to the axis 14. This same arrangement applies equally to all of the arrays 54. Additionally, FIG. 5 indicates that each array 54 will be tilted at an angle β relative to the axis 14 and that each row 56 will include a diffuser 59. Specifically, the diffuser 59 causes light from the individual light sources 58 in a row 56 to diffuse together so that light from a row 56 is incident on the drill bit 12 as a single beam. The diffuser 59 can be of any type well known in the art. Further, recall that each array 54 is paired with another array 54 that are positioned diametrically across the axis 14 from each other. Despite the differences in the angle $\alpha_n$, between different rows 56, all of the individual light sources 58 in an array 54 are directed toward substantially the same point on the axis 14 (e.g. tip 36 of drill bit 12). As intended for the present invention, the individual light sources 58 in the arrays 54 are, preferably, LEDs of a type well known in the pertinent art.

OPERATION

Figure 6:
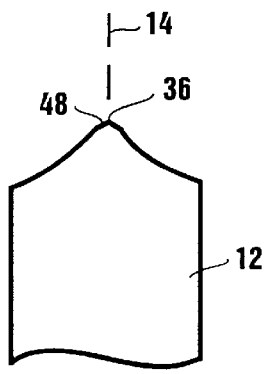
FIG. 6 is a silhouette of the drill bit.

In the operation of the device 10, the drill bit 12 is mounted on a base (not shown) and is advanced in a direction along its longitudinal axis 14 and into an axial position 60 (see FIG. 1). The light source 16 is then activated and the camera 20 receives a silhouette image of the drill bit 12 (see FIG. 6). Based on the actual position of the drill bit 12 as detected by the camera 20, in comparison with the desired position of the drill bit 12, it can be determined how much of the drill bit 12 needs to be moved in order to sharpen the drill bit 12. Further, it can be determined whether the drill bit 12 even has sufficient material remaining for a grinding operation and, if not, whether the drill bit 12 should be discarded.

Figure 7:
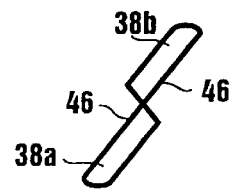
FIG. 7 shows an illumination of the primary facets of the drill bit.

If a grinding operation can be performed, the drill bit 12 is advanced from the axial position 60 into an axial position 62 which effectively corresponds to the coincident focal points of the individual light sources 58 in the light source 22. While the drill bit 12 is in the position 62, a specific row 56 of individual light sources 58 is to be activated. In particular, the row 56 that is activated will depend on the configuration of the drill bit 12. Importantly, the activated row 56 needs to have beam paths 24 at the specific angle $2\alpha_n$ that is required to achieve specular reflections from the primary facets 38a and 38b of the drill bit 12. Using the proper row 56, diametrically opposed pairs of arrays 54 are sequentially activated in order to identify the particular pair of arrays 54 that best illuminate the primary facets 38a and 38b (see FIG. 7). The drill bit 12 can then be rotated about its axis 14 to establish a gross rotational position for the drill bit 12 on the axis 14. Specifically, the extension line 46 can be of considerable use in establishing the gross rotational position.

Figure 8:
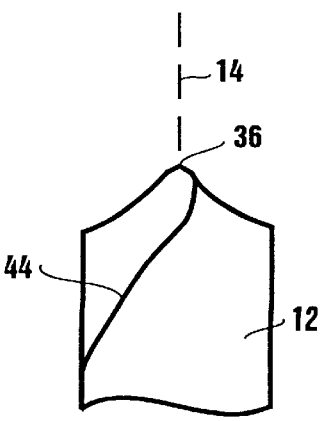
FIG. 8 shows an illumination of a margin of the drill bit.

Once a gross rotational position has been established for the drill bit 12, the drill bit 12 is located in the axial position 60 to achieve even greater precision in the positioning and orientation of the drill bit 12. Specifically, while in the axial position 60, the drill bit 12 is illuminated by the light source 28 to create an image of the margin 44 (see FIG. 8). The image of margin 44 that is created will be observed by the camera 20. Based on the known geometry of the drill bit 12, the image of margin 44 can be used to precisely rotate the drill bit 12, as necessary, into a desired spatial orientation. In this spatial orientation, the drill bit 12 can be moved into a grinding tool (not shown) where the primary facets 38a and 38b are ground down to sharpen the drill bit 12.

Figure 9:
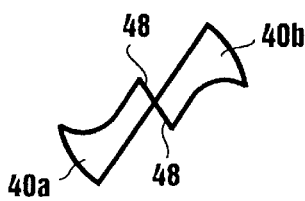
FIG. 9 how illumination of the secondary facets of the drill bit.

After the drill bit 12 has been sharpened, it can be returned to the positions 60 and 62 for inspection. To do this the light source 16 and camera 20 are used to check the profile and axial position of the drill bit 12 in axial position 60. The light source 22 and camera 26 are then used to check the primary facets 38a and 38b with the drill bit 12 in axial position 62. Additionally, the light sources 32a and 32b can be used with camera 26 to check and inspect the secondary facets 40a and 40b (see FIG. 9).

While the particular Optical Inspection Device as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. An optical device for establishing a spatial orientation for a drill bit, the drill bit defining a longitudinal axis and having a primary facet with a normal inclined at an angle $\alpha$ to the axis and having a margin extending generally on a helical path around the axis, said device comprising:
   a first light source for generating a first light beam for silhouetting said drill bit;
   a second light source for generating a second light beam for reflection from said primary facet at an angle of reflection a for travel substantially along said axis, wherein $\alpha=\cos^{-1}(1/\sqrt{(1+\tan^2(\phi)+\tan^2(\psi))})$, and where, in a cartesian coordinate system, $\alpha$ is an angle with the z axis (said longitudinal axis), $\phi$ is an angle of rotation about the x axis, and $\psi$ is an angle of rotation about the y axis;
   a third light source for generating a third light beam for reflection from said margin;
   a means for responding to said first light beam to establish an axial position for the drill bit on said axis;
   a means for responding to said second light beam to establish a gross rotational position for the drill bit on said axis; and
   a means for responding to said third light beam to establish a precise rotational position for the drill bit on said axis to establish said spatial orientation.

2. An optical device as recited in claim 1 wherein said first light source silhouettes said drill bit with said drill bit in a first axial position, said second light source is reflected from said primary facet with said drill bit in a second axial position, and said third light source is reflected from said margin with said drill bit in said first axial position.

3. An optical device as recited in claim 1 wherein said second light source comprises a plurality of arrays, with each array including a plurality of individual light sources arranged in a plurality of rows and said plurality of arrays forming a ring with diametrically opposed pairs of arrays in said ring, said ring being oriented in a plane with each said row in each said array substantially perpendicular to a central axis, and wherein each said light source in each said row directs a respective second light beam toward said axis at a respective angle $2\alpha$ thereto.

4. An optical device as recited in claim 3 wherein each individual light source is an LED.

5. An optical device as recited in claim 3 wherein said first light beam is directed toward the drill bit on a path substantially perpendicular to said axis, and said means for responding to said first light beam is a first camera positioned substantially diametrically opposite the drill bit from said first light source.

6. An optical device as recited in claim 3 wherein said means for responding to said second light beam is a second camera positioned on said axis.

7. An optical device as recited in claim 3 wherein said means for responding to said third light beam is said first camera, and further wherein said third light beam travels from said third light source toward the margin on a transmission path, and is reflected from the margin toward said first camera on a reflection path, with said transmission path and said reflection path forming an angle $\beta$ therebetween.

8. An optical device as recited in claim 3 comprising at least three rows of individual light sources in each said array, including a first row for directing said second beam of light toward the drill bit at an angle $2\alpha_1$ for reflection from a primary facet having a normal inclined at an angle $\alpha_1$ from said axis, a second row for directing said second beam of light toward the drill bit at an angle $2\alpha_2$ for reflection from a primary facet having a normal inclined at an angle $\alpha_2$ from said axis, and a third row for directing said second beam of light toward the drill bit at an angle $2\alpha_3$ for reflection from a primary facet having a normal inclined at an angle $\alpha_3$ from said axis.

9. An optical device as recited in claim 1 wherein said drill bit includes a secondary facet and said device further comprises a fourth light source for generating a fourth light beam with said drill bit in said spatial orientation to illuminate said secondary facet.

10. An optical device for establishing a spatial orientation for a drill bit, the drill bit defining a longitudinal axis and having a primary facet with a normal inclined at an angle $\alpha$ to the axis and having a margin extending generally on a helical path around the axis, said device comprising:

a first light source for generating a first light beam for silhouetting said drill bit with said drill bit in a first axial position;

a second light source for generating a second light beam for reflection from said primary facet at an angle of reflection a for travel substantially along said axis with said drill bit in a second axial position;

a third light source for generating a third light beam for reflection from said margin with said drill bit in said first axial position;

a means for responding to said first light beam to establish an axial position for the drill bit on said axis;

a means for responding to said second light beam to establish a gross rotational position for the drill bit on said axis; and a means for responding to said third light beam to establish a precise rotational position for the drill bit on said axis to establish said spatial orientation.

11. An optical device as recited in claim 10, wherein $\alpha = \cos^{-1}(1/\sqrt{(1+\tan^2(\phi)+\tan^2(\psi))})$, and where, in a cartesian coordinate system, $\alpha$ is an angle with the z axis (said longitudinal axis), $\phi$ is an angle of rotation about the x axis, and $\psi$ is an angle of rotation about the y axis.

12. An optical device as recited in claim 10 wherein said second light source comprises a plurality of arrays, with each array including a plurality of individual light sources arranged in a plurality of rows and said plurality of arrays forming a ring with diametrically opposed pairs of arrays in said ring, said ring being oriented in a plane with each said row in each said array substantially perpendicular to a central axis, and wherein each said light source in each said row directs a respective second light beam toward said axis at a respective angle $2\alpha$ thereto.

13. An optical device as recited in claim 12 comprising at least three rows of individual light sources in each said array, including a first row for directing said second beam of light toward the drill bit at an angle $2\alpha_1$ for reflection from a primary facet having a normal inclined at an angle $\alpha_1$ from said axis, a second row for directing said second beam of light toward the drill bit at an angle $2\alpha_2$ for reflection from a primary facet having a normal inclined at an angle $\alpha_2$ from said axis, and a third row for directing said second beam of light toward the drill bit at an angle $2\alpha_3$ for reflection from a primary facet having a normal inclined at an angle $\alpha_3$ from said axis.

14. An optical device as recited in claim 10 wherein said first light beam is directed toward the drill bit on a path substantially perpendicular to said axis, and said means for responding to said first light beam is a first camera positioned substantially diametrically opposite the drill bit from said first light source, wherein said means for responding to said second light beam is a second camera positioned on said axis, wherein said means for responding to said third light beam is said first camera, and further wherein said third light beam travels from said third light source toward the margin on a transmission path, and is reflected from the margin toward said first camera on a reflection path, with said transmission path and said reflection path forming an angle $\beta$.

15. A method for establishing a spatial orientation for a drill bit, the drill bit defining a longitudinal axis and having a primary facet with a normal inclined at an angle $\alpha$ to the axis and having a margin extending generally on a helical path around the axis, said method comprising the steps of:

generating a first light beam for silhouetting said drill bit with said drill bit in a first axial position;

generating a second light beam for reflection from said primary facet at an angle of reflection $\alpha$ for travel substantially along said axis with said drill bit in a second axial position;

generating a third light beam for reflection from said margin with said drill bit in said first axial position;

responding to said first light beam to establish an axial position for the drill bit on said axis;

responding to said second light beam to establish a gross rotational position for the drill bit on said axis; and responding to said third light beam to establish a precise rotational position for the drill bit on said axis to establish said spatial orientation.

16. A method as recited in claim 15, wherein $\alpha = \cos^{-1}(1/\sqrt{(1+\tan^2(\phi)+\tan^2(\psi))})$, and where, in a Cartesian coordinate system, $\alpha$ a is an angle with the z axis (said longitudinal axis), $\phi$ is an angle of rotation about the x axis, and $\psi$ is an angle of rotation about the y axis.

17. A method as recited in claim 15 wherein said second light source comprises a plurality of arrays, with each array including a plurality of individual light sources arranged in a plurality of rows and said plurality of arrays forming a ring with diametrically opposed pairs of arrays in said ring, said ring being oriented in a plane with each said row in each said array substantially perpendicular to a central axis, and wherein each said light source in each said row directs a respective second light beam toward said axis at a respective angle $2\alpha$ thereto.

18. A method as recited in claim 17 comprising at least three rows of individual light sources in each said array, including a first row for directing said second beam of light toward the drill bit at an angle $2\alpha_1$ for reflection from a primary facet having a normal inclined at an angle $\alpha_1$ from said axis, a second row for directing said second beam of light toward the drill bit at an angle $2\alpha_2$ for reflection from a primary facet having a normal inclined at an angle $\alpha_2$ from said axis, and a third row for directing said second beam of light toward the drill bit at an angle $2\alpha_3$ for reflection from a primary facet having a normal inclined at an angle $\alpha_3$ from said axis.

19. A method as recited in claim 18 wherein each individual light source is an LED.

20. A method as recited in claim 15 further comprising the steps of:

directing said first light beam toward said drill bit on a path substantially perpendicular to said axis, and wherein said step of responding to said first light beam is accomplished using a first camera positioned substantially diametrically opposite the drill bit from said first light source;

positioning a second camera on said axis for responding to said second light beam; and directing said third light beam from said third light source toward the margin on a transmission path for reflection from the margin toward said first camera on a reflection path for responding to said third light beam, with said transmission path and said reflection path forming an angle $\beta$ therebetween.

* * * * *

UNITED STATES PATENT AND TRADEMARK OFFICE
CERTIFICATE OF CORRECTION

PATENT NO. : 6,191,856 B1
DATED : February 20, 2001
INVENTOR(S) : Charles S. Slemon, W. James Frandsen, James John Glover It is certified that error appears in the above-identified patent and that said Letters Patent is hereby corrected as shown below:

Column 1,
Line 3, delete [continuation-part], insert -- continuation-in-part --

Column 3,
Line 65, delete [$2\alpha_2$], insert -- $2\alpha_1$ --

Column 4,
Line 5, delete [$\alpha_2$], insert -- $2\alpha_2$ --
Line 23, delete [$\pm 40°$], insert -- $\pm 4°$ --
Line 28, delete [$\pm 0.250°$], insert -- $\pm 0.25°$ --
Line 61, delete [how], insert -- shows --

Column 6,
Line 2, delete [$\cos_{-1}$], insert -- $\cos^{-1}$ --

Column 8,
Line 8, delete [a], insert -- $\alpha$ --

Column 9,
Line 15, delete [a], insert -- $\alpha$ --

UNITED STATES PATENT AND TRADEMARK OFFICE
CERTIFICATE OF CORRECTION

PATENT NO. : 6,191,856 B1
DATED : February 20, 2001
INVENTOR(S) : Charles S. Slemon, W. James Frandsen, James John Glover It is certified that error appears in the above-identified patent and that said Letters Patent is hereby corrected as shown below:

Column 10,
Line 24, delete [a]

Signed and Sealed this

Seventh Day of August, 2001

*Attest:*

*Attesting Officer*

NICHOLAS P. GODICI
*Acting Director of the United States Patent and Trademark Office*